US 9,452,072 B2

(12) United States Patent
Provenza (10) Patent No.: US 9,452,072 B2
(45) Date of Patent: Sep. 27, 2016

(54) APPARATUS AND METHODS FOR ANCHORING IN THE STOMACH AND THE DUODENUM

(71) Applicant: J. Mark Provenza, Shreveport, LA (US)

(72) Inventor: J. Mark Provenza, Shreveport, LA (US)

(*) Notice: Subject to any disclaimer, the term of this patent is extended or adjusted under 35 U.S.C. 154(b) by 183 days.

(21) Appl. No.: 14/310,993

(22) Filed: Jun. 20, 2014

(65) Prior Publication Data
US 2014/0378884 A1     Dec. 25, 2014

Related U.S. Application Data

(60) Provisional application No. 61/839,174, filed on Jun. 25, 2013.

(51) Int. Cl.
*A61M 5/00* (2006.01)
*A61F 5/00* (2006.01)

(52) U.S. Cl.
CPC ............ *A61F 5/003* (2013.01); *A61F 5/0036* (2013.01); *A61F 5/0076* (2013.01)

(58) Field of Classification Search
CPC ..... A61F 5/0076; A61F 5/0079; A61F 5/003
See application file for complete search history.

(56) References Cited

U.S. PATENT DOCUMENTS

| 4,878,905 | A | 11/1989 | Blass |
| 7,695,446 | B2 | 4/2010 | Levine et al. |
| 7,976,488 | B2 | 7/2011 | Levine et al. |
| 8,118,774 | B2 | 2/2012 | Dann et al. |
| 8,147,561 | B2 | 4/2012 | Binmoeller |
| 8,303,669 | B2 | 11/2012 | Meade et al. |
| 8,403,877 | B2 | 3/2013 | Priplata et al. |
| 2009/0275960 | A1 | 11/2009 | Provenza et al. |
| 2011/0004228 | A1* | 1/2011 | Priplata ............. A61B 17/3468 606/153 |
| 2011/0066175 | A1 | 3/2011 | Gross |
| 2012/0095385 | A1 | 4/2012 | Dominguez et al. |
| 2013/0079603 | A1 | 3/2013 | Vargas |
| 2013/0310727 | A1* | 11/2013 | Stack ....................... A61F 2/04 604/9 |

OTHER PUBLICATIONS

International search report and written opinion dated Nov. 4, 2014 for PCT/US2014/043967.

* cited by examiner

*Primary Examiner* — Leslie Deak
(74) *Attorney, Agent, or Firm* — Wilson Sonsini Goodrich & Rosati (57) ABSTRACT

A suprapyloric anchor assembly includes an antral cap having at least three stabilizing members configured to reside in an antrum and engage tissue circumscribing a pyloric valve. A duodenal member is configured to reside at least partially in a duodenal bulb, and one or more tethers connect the antral cap to the duodenal member. The tether(s) is/are configured to allow passage of stomach contents through the pyloric valve. Optionally, one or more gastric balloon(s) may attached to the suprapyloric anchor and be inflated with the gastric cavity.

13 Claims, 13 Drawing Sheets

APPARATUS AND METHODS FOR ANCHORING IN THE STOMACH AND THE DUODENUM

CROSS-REFERENCE TO RELATED APPLICATION

This application claims the benefit of provisional application 61/839,174, filed on Jun. 25, 2013, the full disclosure of which is incorporated herein by reference.

BACKGROUND OF THE INVENTION

1. Field of the Invention

The present invention relates generally to medical devices and methods and more particularly to the endoscopic treatment of obesity.

Obesity is one of the leading preventable causes of death worldwide and has become a global epidemic affecting more than 400 million people. In the United States alone, approximately 300,000 obesity-linked deaths occur annually, and obesity-related co-morbidities lead to nearly $150 billion in healthcare spending. Obesity is a medical condition associated with many subsequent diseases, including type-2 diabetes, cardiovascular disease, sleep apnea and certain types of cancer. These conditions often have severe adverse effects on overall health, reduce quality of life, limit productivity, lead to significant medical costs, and can ultimately lead to reduced life expectancy.

The primary treatment for obesity is dieting, routine physical exercise, and in some cases pharmacologic therapy. Obesity surgery, including gastric bypass laparoscopic banding, involves surgical restriction of the stomach to reduce the caloric intake of the patient by triggering the satiety impulse more rapidly, physically remove the ability of the individual to ingest more than a limited amount of food, and/or inhibit the ability of the individual's digestive system to extract the full caloric value of the food being eaten.

Such surgical treatments for obesity, although often effective in achieving sustainable weight loss, involve gross anatomical reconstruction of the digestive system, which may be irreversible. Unfortunately, such surgeries can cause significant adverse events, complications, and/or mortality. Thus, there is a growing need for effective and safe alternatives to obesity surgery for the obese patient population worldwide.

Type 2 diabetes is a disorder that is characterized by high blood glucose resulting from insulin resistance and relative insulin deficiency. There are approximately 30 million diabetics in the U.S., 90% of whom are type-2. Traditionally considered a disease of adults, type 2 diabetes is increasingly diagnosed in children in parallel to rising obesity rates due to alterations in dietary patterns as well as in life styles during childhood.

Type 2 diabetes is a chronic, progressive disease that has no established cure, but does have well-established treatments which can delay or mitigate the inevitable consequences of the condition. Type 2 diabetes is initially treated by adjustments in diet and exercise, and by weight loss, most especially in obese patients.

Endoscopic and other minimally invasive procedures have been proposed for treating both obesity and type-2 diabetes. For example, gastric balloons may be implanted for extended periods of time and can reduce patient appetite leading to weight loss. Alternatively, duodenal sleeves may be placed in the upper duodenum to reduce nutrient uptake, also leading to weight loss and possibly having a more direct impact on blood sugar levels and diabetes.

While very promising, the use of both gastric balloons and duodenal sleeves is limited by the difficulty of anchoring the one or more balloon(s) and/or the sleeve within the target anatomy. In particular, it is very difficult to staple or otherwise attach one or more balloon(s) within the stomach. Introduction and removal of both gastric balloons and duodenal sleeves can also be problematic.

For these reasons, it would be desirable to provide improved gastric balloon and/or duodenal sleeve anchoring systems and methods for their deployment. It would be particularly desirable to provide improved anchors capable of stably maintaining one or more gastric balloon(s) and/or a duodenal sleeve in the stomach and/or duodenum for extended periods of time. Such anchoring systems should be compatible with a variety or endoscopic introduction and removal systems and should preferably be capable of introduction in a low profile configuration where they self-expand to a deployed configuration when released in the stomach and/or duodenum. The following inventions will meet at least some of these objectives.

2. Description of the Background Art

Devices which anchor in or around the pyloric valve are described in U.S. Pat. No. 4,878,905; U.S. Pat. No. 8,147,561; U.S. Pat. No. 8,403,877; US 2011/0066175; and US 2012/0095385.

SUMMARY OF THE INVENTION

In a first aspect of the present invention, a suprapyloric anchor assembly comprises an antral cap having at least three stabilizing members configured to reside in an antrum and engage tissue circumscribing a pyloric valve. A duodenal member is configured to reside at least partially in a duodenal bulb, and one or more tethers connect the antral cap to the duodenal member. The tether(s) is/are configured to allow passage of stomach contents through the pyloric valve.

In specific aspects of the assembly, the antral cap comprises a collar with a central passage, and the stabilizing members comprise elongate legs joined to the collar at their proximal ends. The elongate legs preferably have atraumatic distal ends which engage the tissue circumscribing the pyloric valve when the legs are deployed radially outwardly. Typically, the legs are spring-mounted (self-opening) at their proximal ends to the collar so that the legs may be radially constrained to have a reduced collective diameter to facilitate introduction and may be released from constraint to assume a deployed (radially outward relative to a center axis of the anchor) configuration where the atraumatic distal ends are spaced-apart from each other. In still further specific aspects, the duodenal member may comprise a funnel section configured to reside in the duodenal bulb and a cylindrical sleeve membrane configured to reside in the duodenum below the duodenal bulb. Specific system configurations may further comprise one or more gastric balloon(s) connectable to the antral cap.

In a second aspect of the present invention, a method for deploying a suprapyloric anchor comprises providing a suprapyloric anchor including an antral cap connected to a duodenal member by one or more tethers. The suprapyloric anchor is endoscopically introduced with three constrained stabilizing members. The duodenal member is positioned in a duodenal bulb with the tethers passing through a pyloric valve. The duodenal member is released in a duodenal bulb with the tethers passing through a pyloric valve. The expanded stabilizing members are engaged against tissue circumscribing the pyloric valve such that the duodenal member is tensioned to hold the stabilizing members against the circumscribing tissue.

In specific aspects of the method, one or more gastric balloon(s) attached to the suprapyloric anchor is inflated with the gastric cavity (stomach). Optionally, a duodenal sleeve attached to the suprapyloric anchor may be deployed in the duodenum. The one or more gastric balloon(s) act to decrease the effective volume of the stomach to induce a feeling of satiety in the patient, and the duodenal sleeve acts to reduce the absorption of nutrients to decrease caloric intake by the patient. In the exemplary embodiments, the suprapyloric anchor is endoscopically introduced, typically while located coaxially over an endoscope. The anchor and endoscope will usually be passed through an overtube which has been transesophageally introduced into the gastric cavity.

These and other aspects and features of the present invention will become apparent to those of ordinary skill in the art upon review of the following description of specific embodiments of the invention in conjunction with the accompanying figures.

DETAILED DESCRIPTION OF THE INVENTION

The following reference numbers are used herein: 10—gastroscope; 12—duodenal impermeable membrane; 13—elastic retention ring; 14—elastic ring string; 15—forceps (via scope); 16—overtube; 17—bulb funnel; 18—duodenal straps/tethers; 19—anchor legs (tripod); 20—antral anchor cap; 21—balloon cap; 22—superior balloon inflation valve; 23—superior balloon inflation chamber/tube; 14—catheter (via scope); 25—inferior balloon valve; 26—inferior balloon inflation chamber/tube; 27—balloon cap swivel joint; 28—balloon cap disengagement port; 29—balloon support w/inflation chambers; 30—inferior balloon; 31—inferior balloon inflation port; 32—superior balloon chamber; 33—superior balloon; 34—superior balloon port; 35—antral anchor foot base; 36—silicone gel pads; 37—flexible antral foot joint; 38—catheter (via scope); 39—endoscopic balloon (inflated); 40—duodenum; 41—duodenal bulb; 42—pylorus; 44—gastric antrum; 45—gastric angularis; 46—gastric lesser curve; 47—gastric cardia; 48—gastric fundus; 49—gastric greater curve; 50—lower esophageal sphincter; 51—esophagus (distal); 62—small bowel barrier/membrane wrap (removable); 63—small bowel barrier/membrane (compressed and contained within overlying wrap); 63a—small bowel barrier/membrane (released by removing/pulling out the wrap); 63b—small bowel barrier/membrane (spontaneously opening); 63c—small bowel barrier/membrane (further spontaneous and propulsive extension); 64—duodenal bulb barrier/membrane funnel (released within the duodenal bulb); 65—elastic binding ring (unbound); 65b—elastic binding ring (bound); 66—silicone gel footpad; 66a—silicone gel footpad (non-compressed); 66b—silicone gel footpad (compressed); 67—strap/tether attached to the inner diameter of the bulb funnel (64); 68—inner tube which allows gastroscope (1) to pass; 69—outer tube which compresses antral anchor components; 70—antal anchor cap; 71—balloon cap; 72—anchor leg (a tripod leg); 73—balloon (one or more balloons may be used); 74—pyloric sphincter; 76—compressible antral anchor lower leg; and 77—compression spring.

Figure 1:
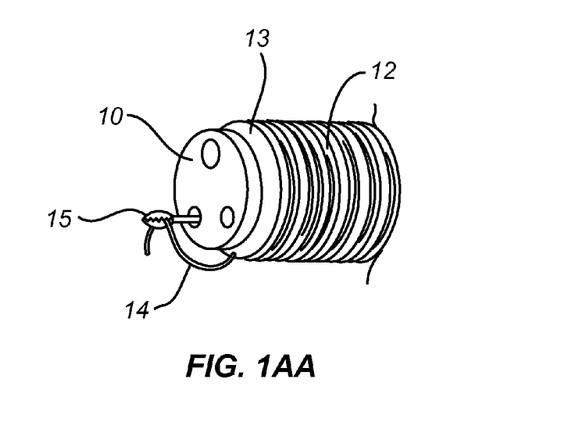
Figure 1A:
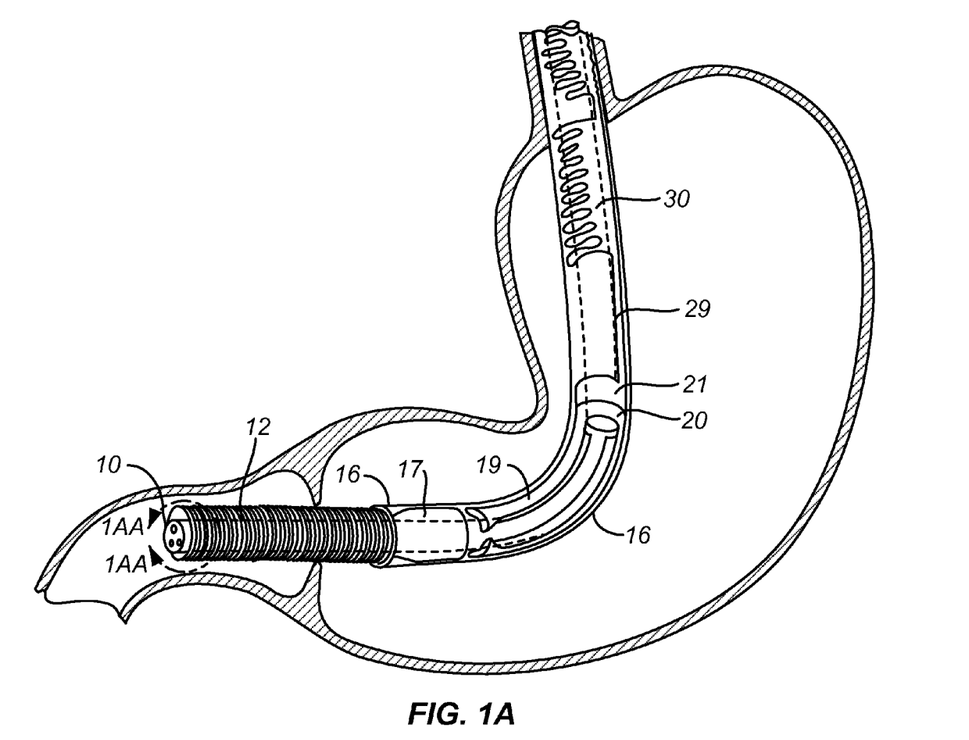
FIGS. 1A and 1AA illustrate a first exemplary embodiment of a suprapyloric anchor assembly constructed in accordance with the principles of the present invention.

FIGS. 1A and 1AA illustrate the device components contained within a delivery overtube (16). A standard adult gastroscope (10) is preloaded by traversing the core of the system. A duodenal impermeable membrane (12) is bunched up at the end of the scope held on the scope tip by an elastic retention ring (13) to prevent premature deployment. A standard gastroscope forceps (15) grasps an elastic ring string (14) for later release.

Figure 1B:
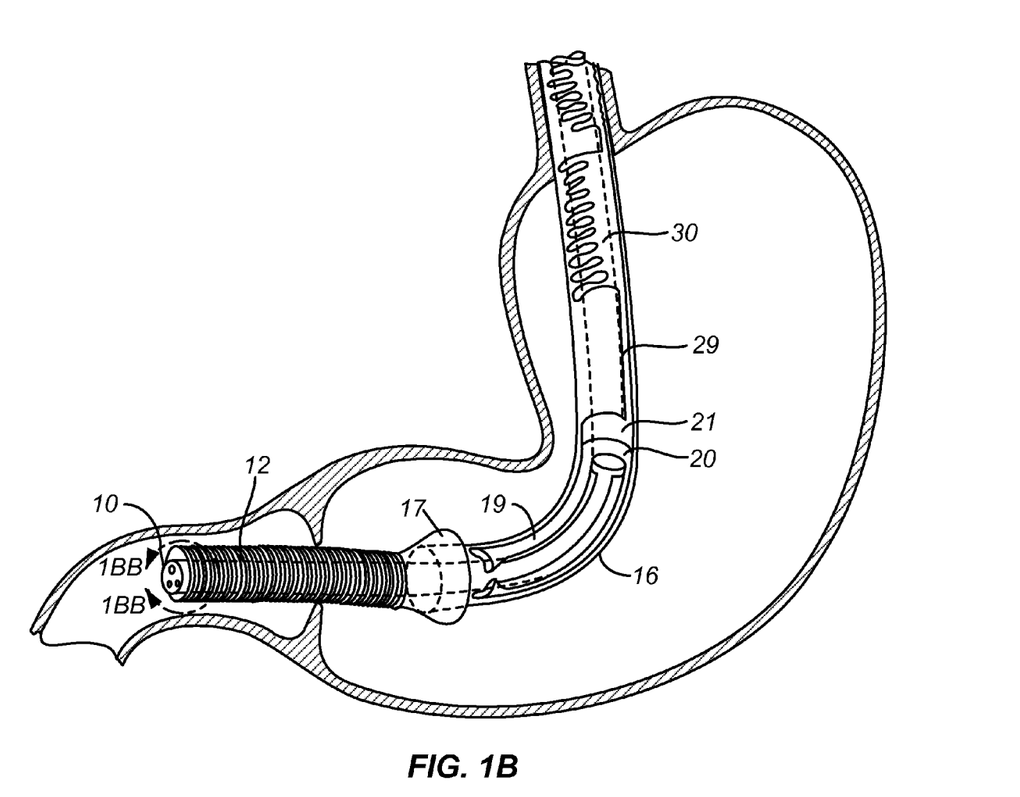
FIGS. 1B and 1BB illustrate a second exemplary embodiment of a suprapyloric anchor assembly constructed in accordance with the principles of the present invention.

FIGS. 1B and 1BB illustrate a system similar to that of FIGS. 1A and 1AA with a bulb funnel (17) positioned over the distal end of the overtube (16) rather than inside of the distal end of the overtube 1(6).

Figure 2A:
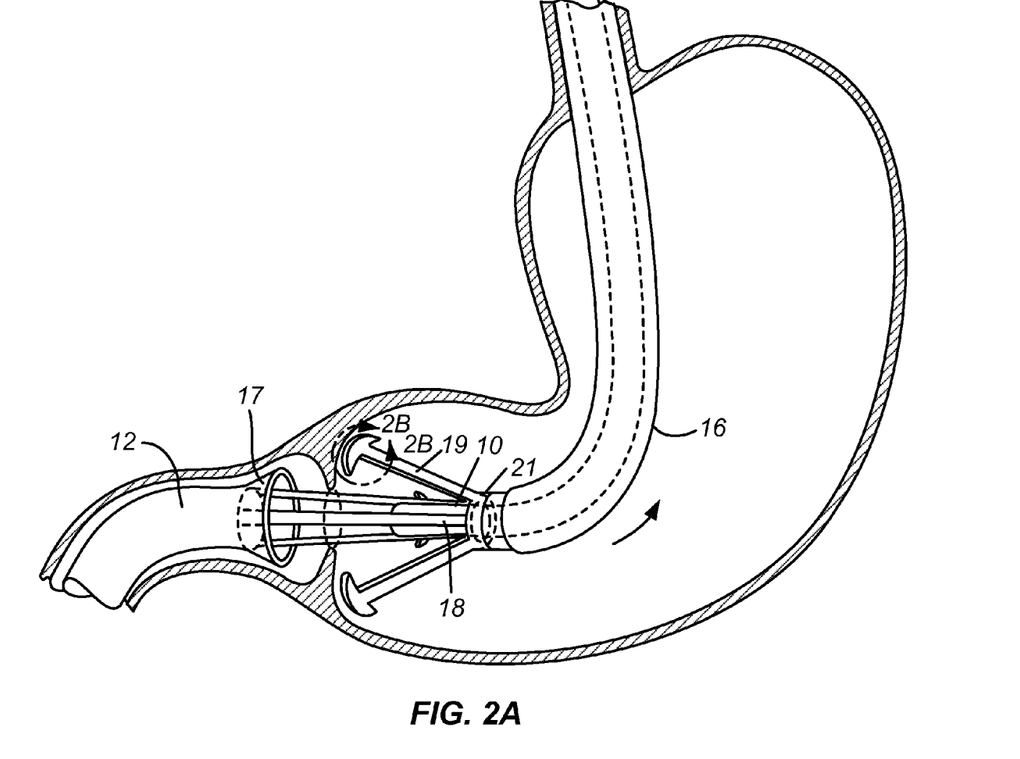
FIGS. 2A and 2B illustrate the deployment of a tripod anchor of the suprapyloric anchor assembly in accordance with the principles of the present invention.
Figure 2B:
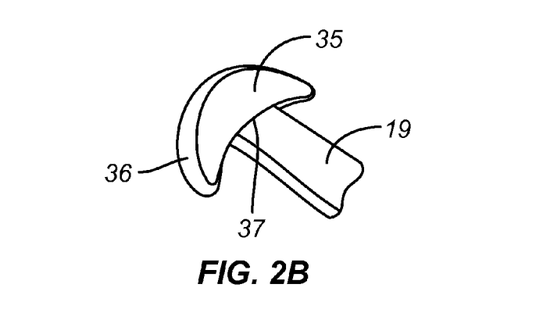

FIGS. 2A and 2B illustrate release of a bariatric component as the overtube (16) is retracted. The gastroscope (10) allows the operator to visually observe the deployment. Three duodenal straps (18) are each attached at one end to the bottom of an antral anchor (21) and at the other end to a junction between the membrane (12) and the bulb funnel (17). An anchor comprises three anchor legs (19) (forming a tripod) each of which is attached to a foot base (35) by a flexible or pivotable joint (37). The foot bases (35) may comprise silicone gel pads (36) to provide atraumatic contact to the stomach surface. As illustrated in FIGS. 2A and 2B, the tripod legs have expanded to their unconstrained configuration once the overtube (16) has been retracted, releasing them from their constrained configurations. It may in some cases be preferable to preload the bulb funnel (17) outside the overtube (16).

Figure 3A:
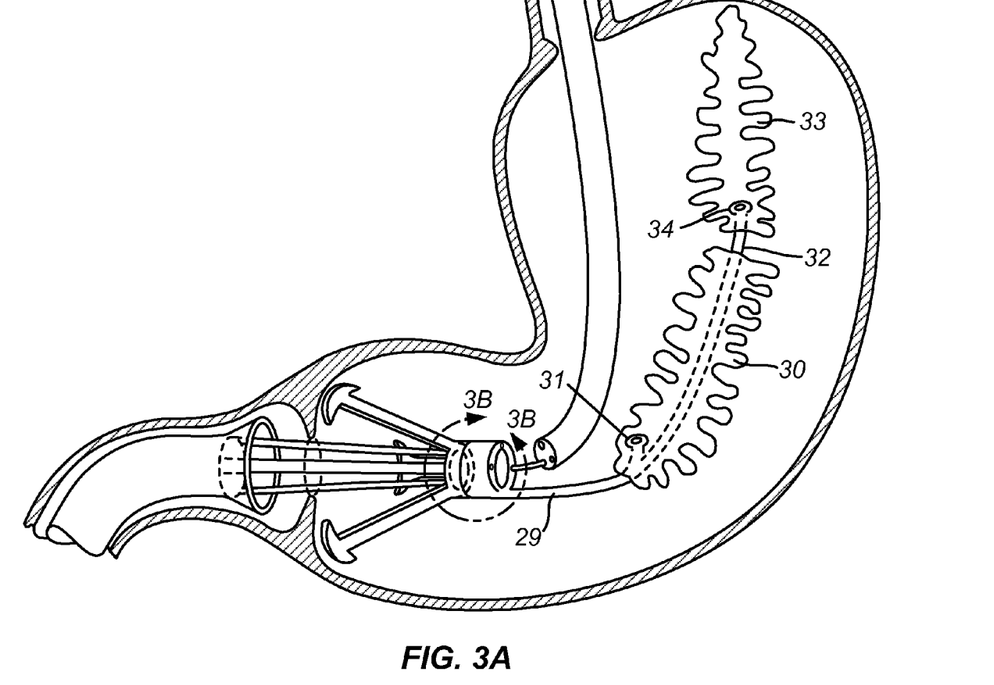
FIGS. 3A and 3B illustrate full deployment of the suprapyloric anchor assembly including an antral anchor, a bulb funnel, a duodenal membrane, and uninflated gastric balloons in accordance with the principles of the present invention.
Figure 3B:
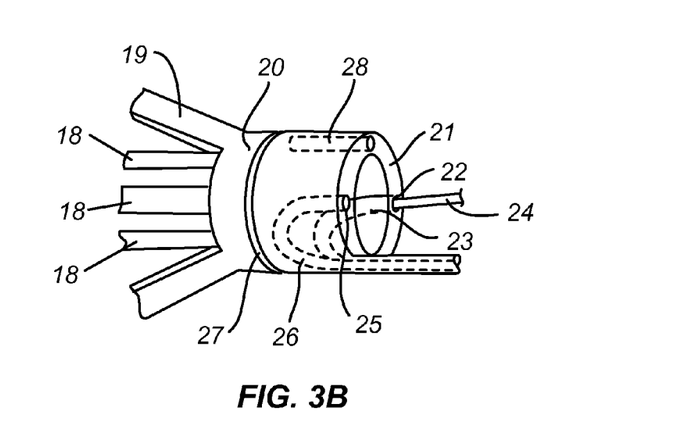

FIGS. 3A and 3B illustrates full release of the bariatric components. Two uninflated balloons (30 and 33) are in the process of being inflated via a scope catheter (24) inserted into a superior balloon port (22). An inferior balloon port (25) is located opposite to the superior balloon port on the rim of balloon cap (21). The balloons may be filled with either air or water, and inflation can be adjusted to add or remove volume. A balloon cap disengagement port (28) can be depressed with a catheter to either remove or replace the balloons. The balloon cap can rotate or swivel via a joint (27) between the antral anchor cap (20) and balloon cap (21).

Figure 4:
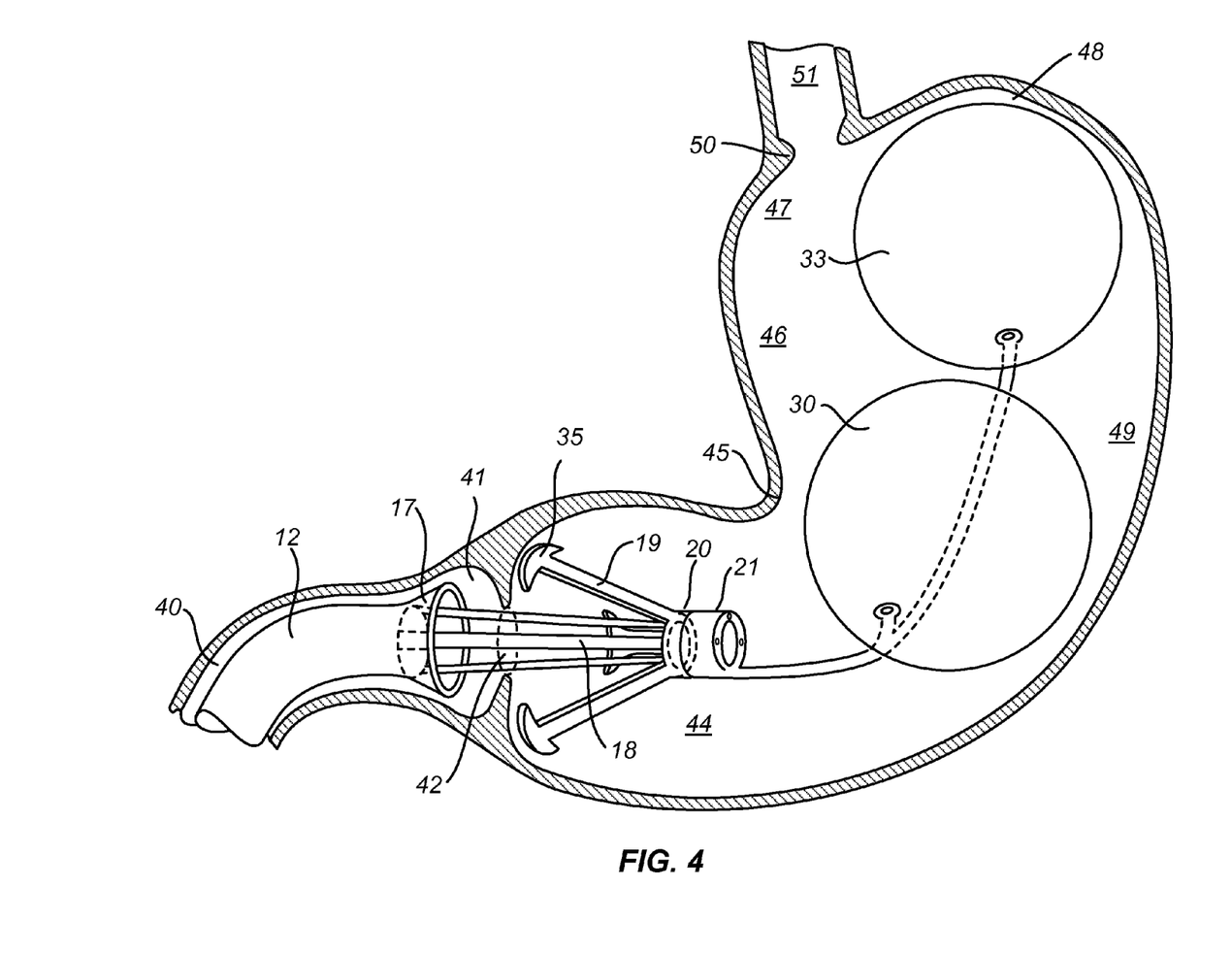
FIG. 4 illustrates inflation of the gastric balloons in accordance with the principles of the present invention.

FIG. 4 illustrates full deployment and removal of the delivery system. The superior balloon (33) is inflatable to 7-9 cm diameter (180-382 cc volume) and the inferior balloon (30) is expandable to 8-10 cm dia. (268-523 cc vol.). The duodenal membrane (12) is 60 cm in length.

Figure 5:
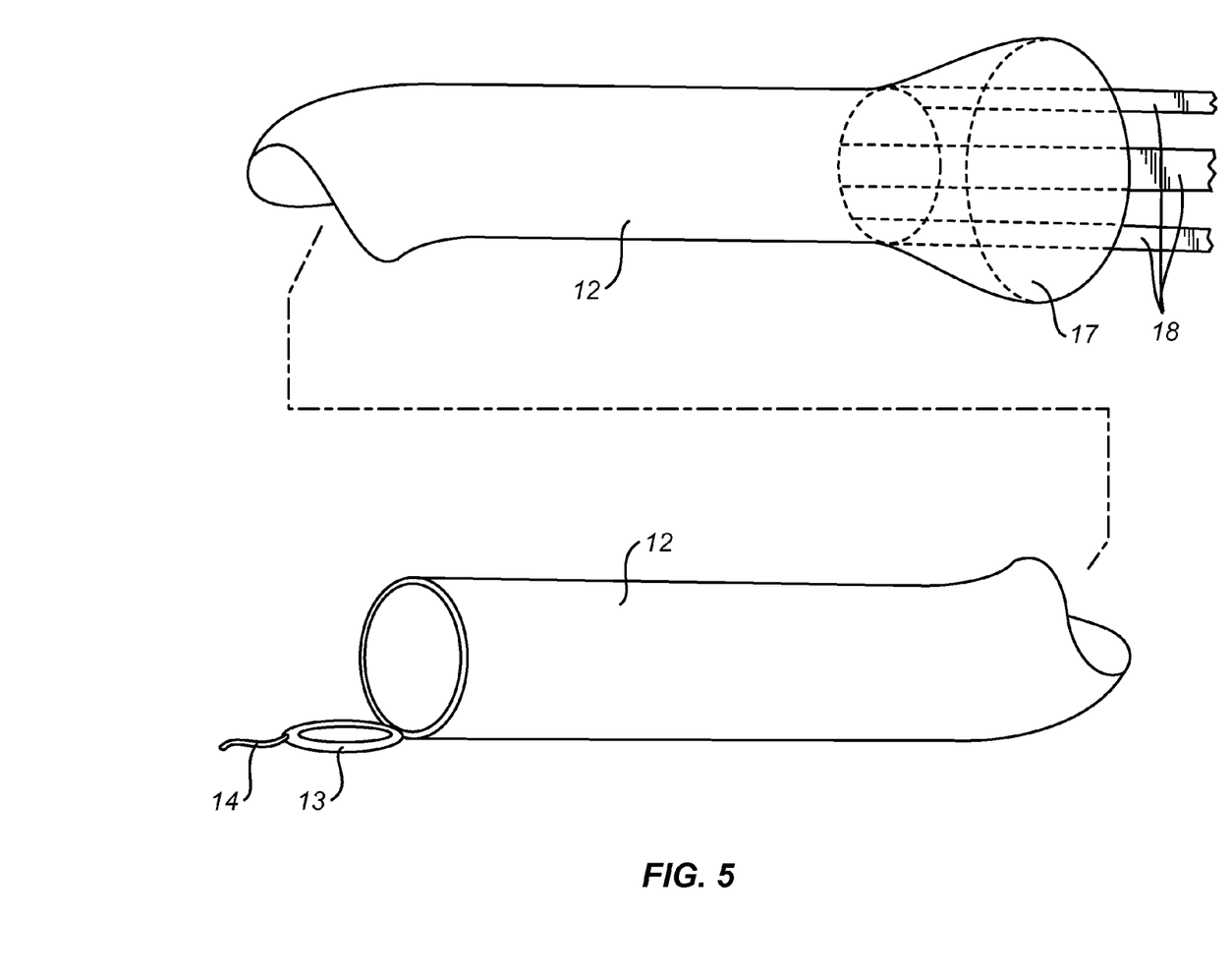
FIG. 5 is a detailed view of the end of a membrane and elastic release elastic ring.

FIG. 5 illustrates the detail of the end of the duodenal membrane (12) which may be formed from a fluropolymer. The released elastic ring (13) is attached to membrane. The ring also serves as a weight which may assist in the small bowel propagation of the 60 cm membrane.

Figure 6:
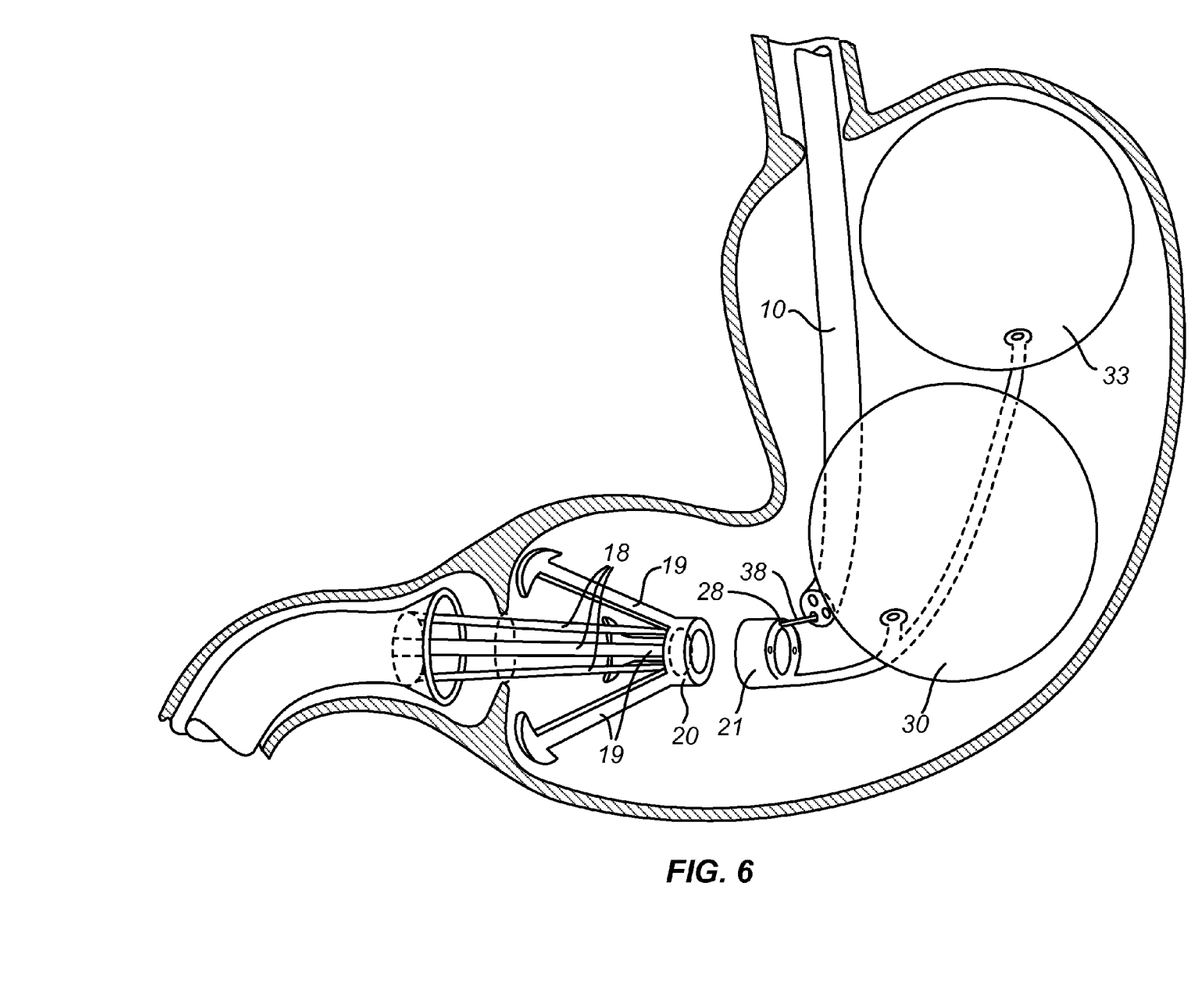
FIG. 6 illustrates preparation for balloon removal.

FIG. 6 illustrates the initial steps for balloon removal. A catheter (38) is inserted into the balloon cap release port (28) releasing the balloon cap (21) from the antral anchor (20). The balloons (30 and 33) can be deflated by either puncture or volume removal via the balloon ports (22 and 25).

Figure 7:
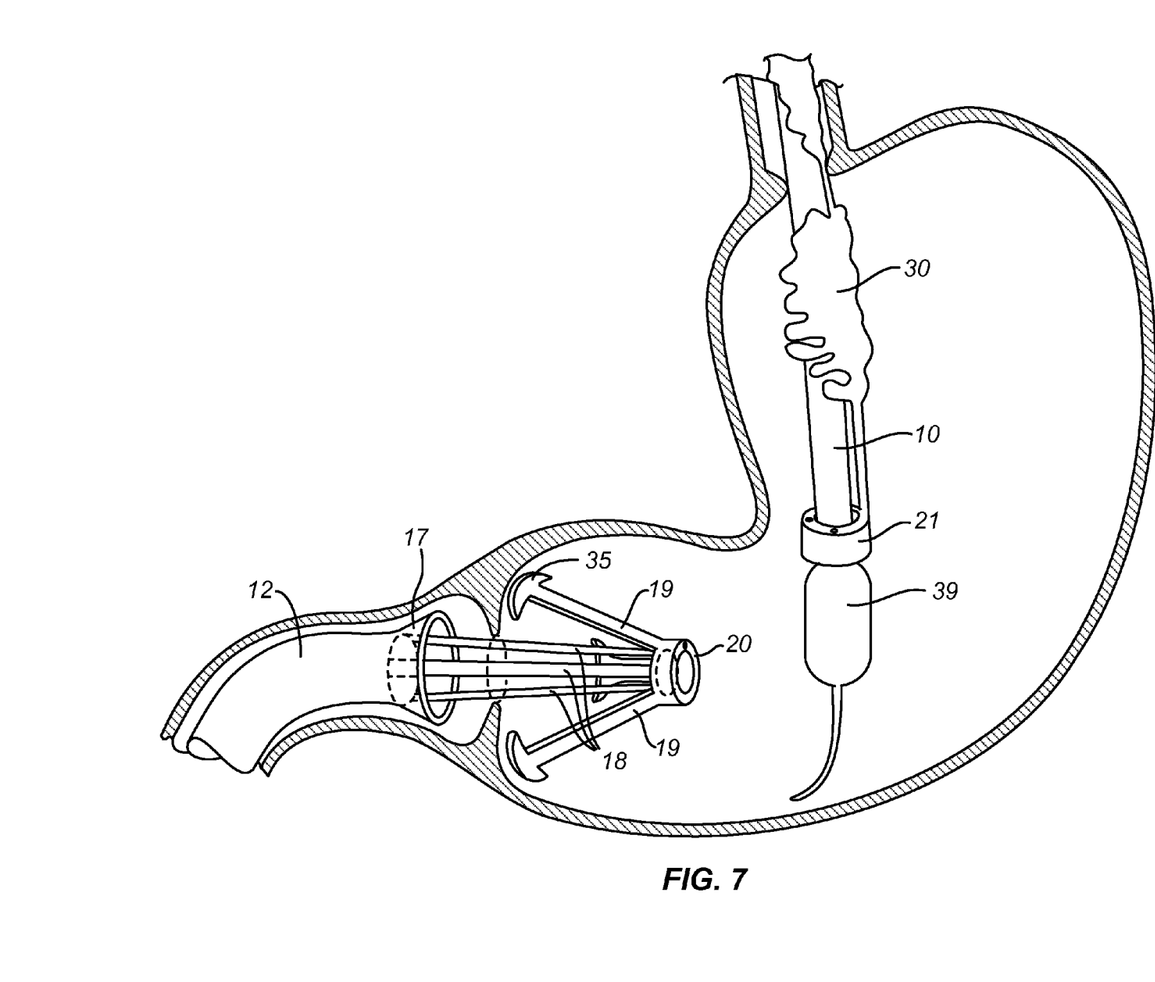
FIG. 7 illustrates removal of the balloon system using a gastroscope.

FIG. 7 illustrates further steps for removal of the balloon system using a standard gastroscope (10) in a through-the-scope (TTS) balloon (39). The balloon is typically 17 mm (54 French). The deflated TTS balloon (39) is advanced through the bariatric balloon cap (21), and the TTS balloon is then inflated using standard endoscopy equipment. The cap (21) and balloons (30 and 33) are removed by withdrawing the scope (10) through the esophagus (51) and mouth.

Figure 8:
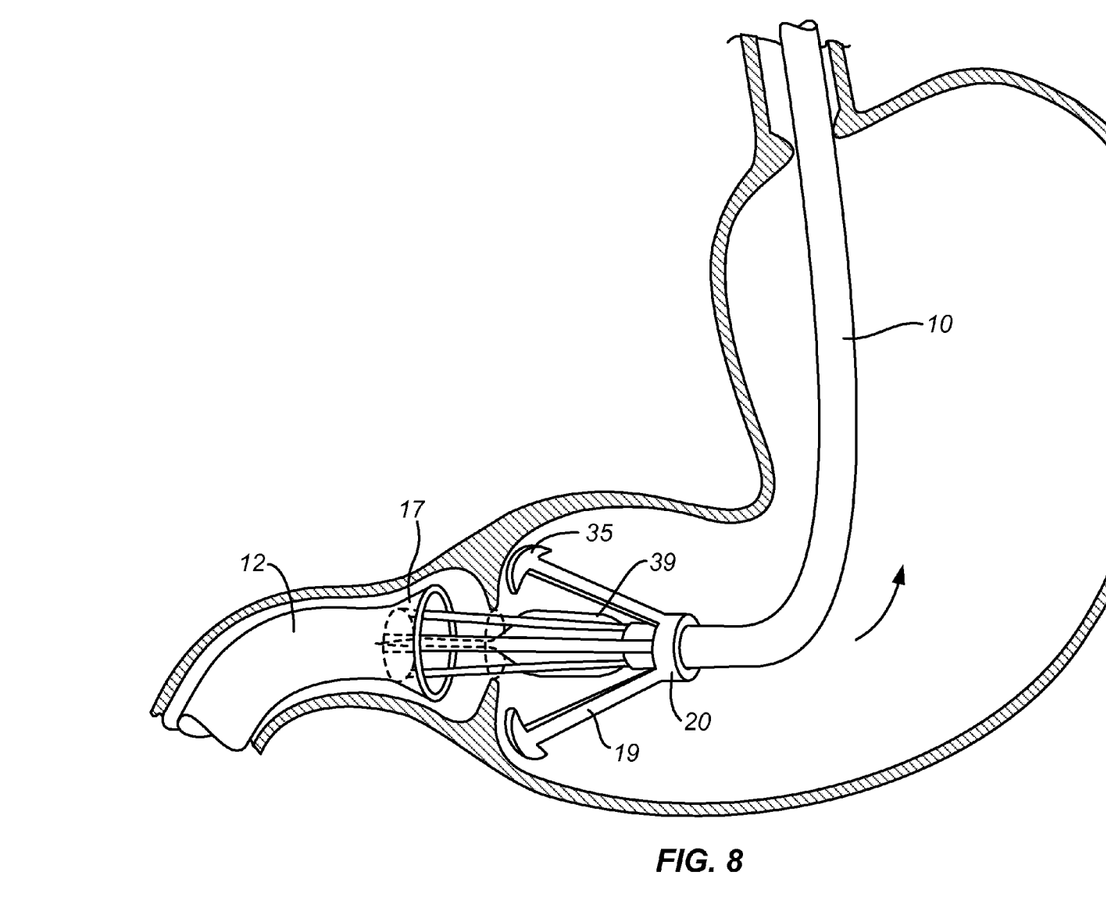
FIG. 8 illustrates further removal of the antral anchor, the bulb funnel, and the duodenal membrane.

FIG. 8 illustrates removal of the antral anchor (20), bulb funnel (17), and duodenal membrane (12) using the same techniques shown in FIG. 7.

Figure 9:
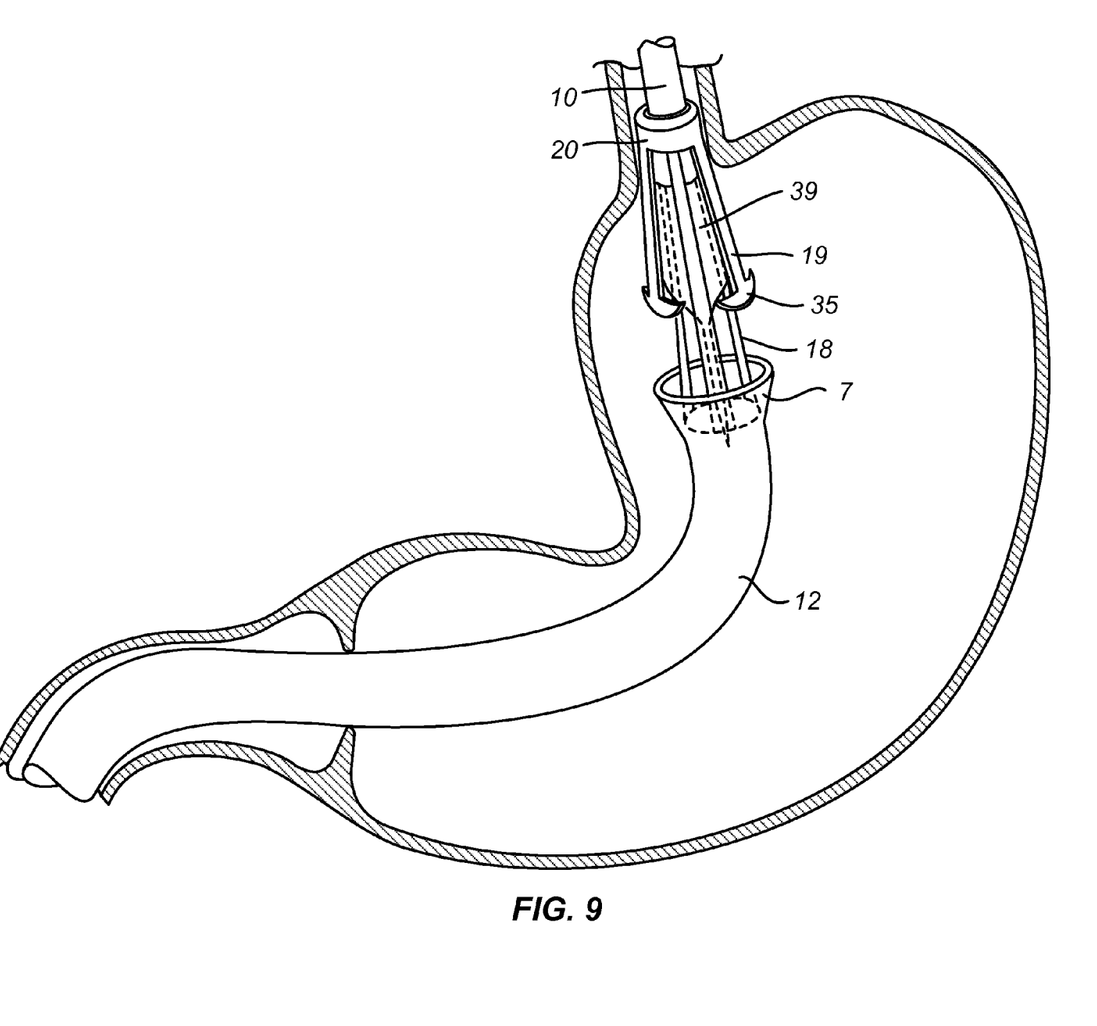
FIG. 9 illustrates final removal progression of the the antral anchor, the bulb funnel, and the duodenal membrane as the scope is withdrawn.
Figure 10A:
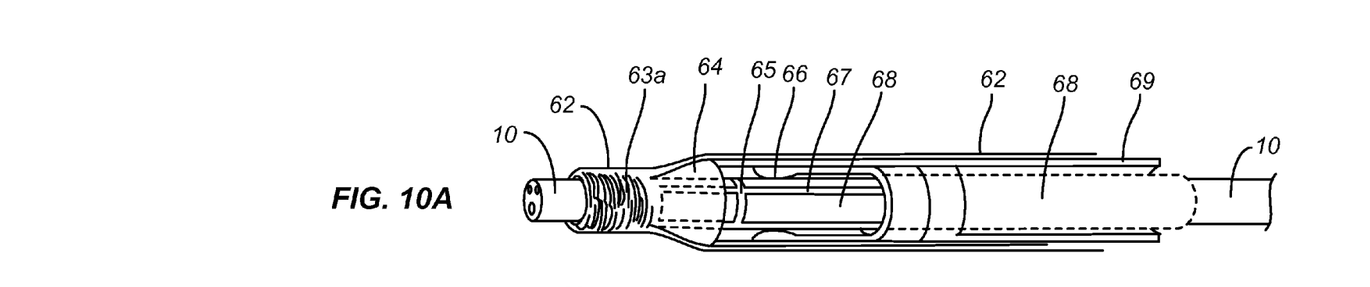
FIGS. 10A through 10D illustrate a further exemplary embodiment of a suprapyloric anchor assembly having constrained tethers constructed in accordance with the principles of the present invention.
Figures 10B, 10C:
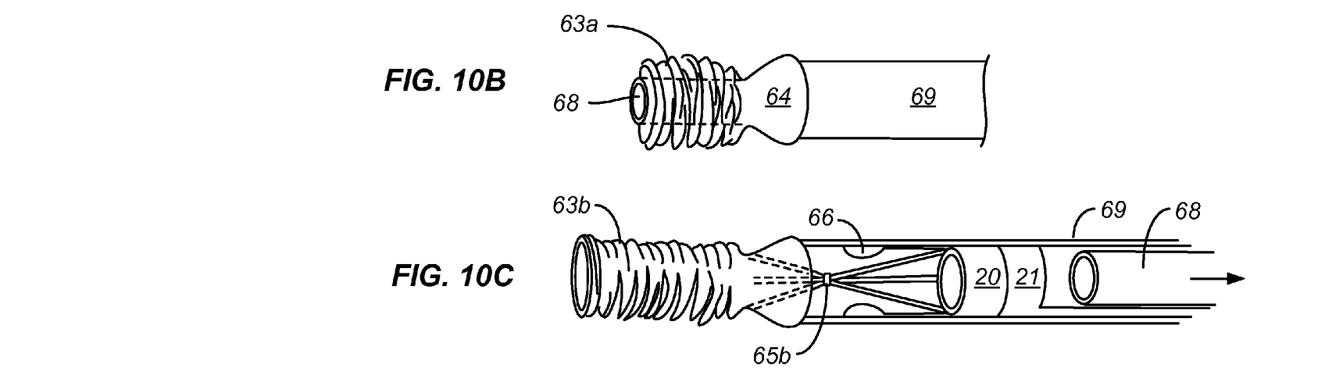
Figure 10D:
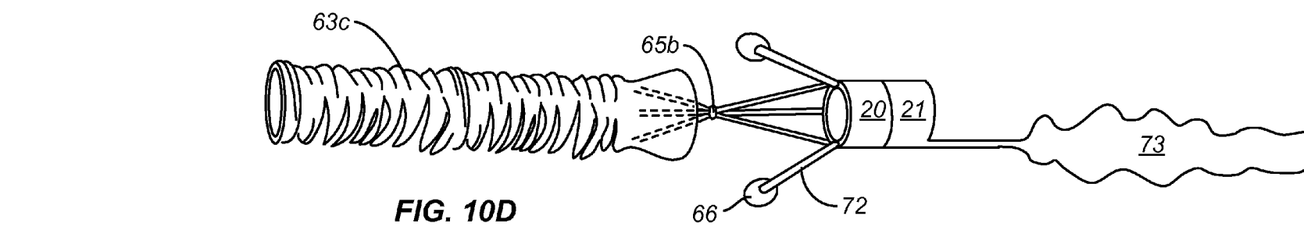

FIG. 9 illustrates the removal progression of the antral anchor (20), bulb funnel (17), and duodenal membrane (12) as the scope (10) and TTS balloon (39) are being withdrawn. The tripod anchor legs (19) and anchor foot bases (35) passively collapse as they are pulled through a narrow space i.e. esophagus. The bulb funnel (17) may evert upon withdrawal through the more narrow esophagus. The balloon cap system (21, 30, and 33) and antral anchor system (20, 17, and 12) may be removed with method above; however, both systems may be also pulled into an overtube as alternative method.

FIGS. 10A-10D illustrate an alternative delivery system and method with sequential removal of a wrap (62), the gastroscope (10), the inner tube (68), and the outer tube (69). In contrast to previously described embodiments, an elastic binding ring 65 (FIGS. 10C and 10D) constrains tethers 67 to reduce potential obstruction of or interference with the pyloris when the system is deployed. The membrane is constrained by the wrap (62) which extends over the overtube and is pulled back to release the membrane. A pull back of 5 cm to 10 cm may be sufficient to release the bundled membrane.

Figure 11A:
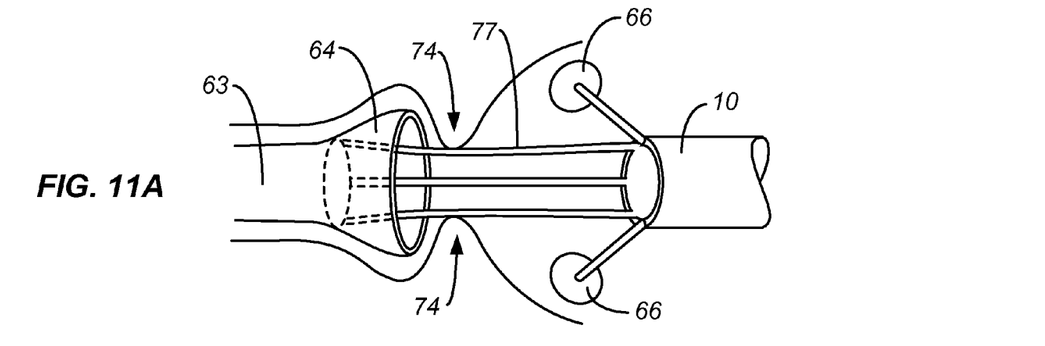
FIGS. 11A through 11D further illustrate the constrained tethers of FIGS. 10A through 10D.
Figure 11B:
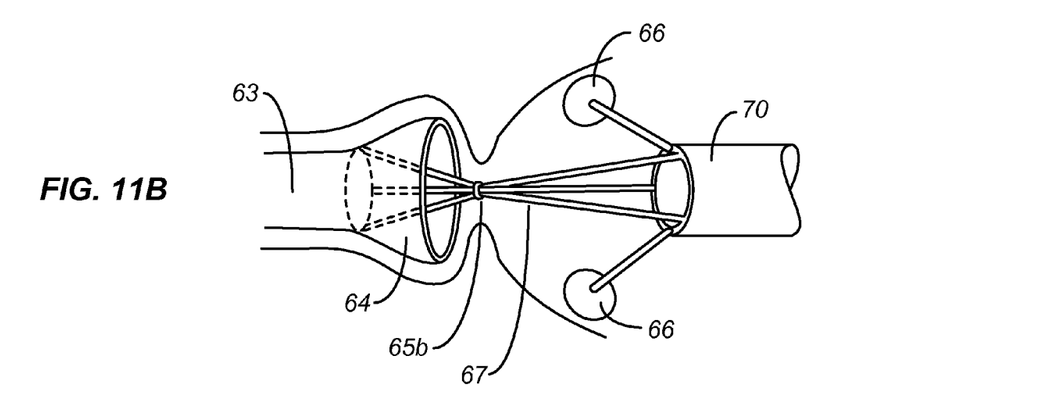
Figure 11C:
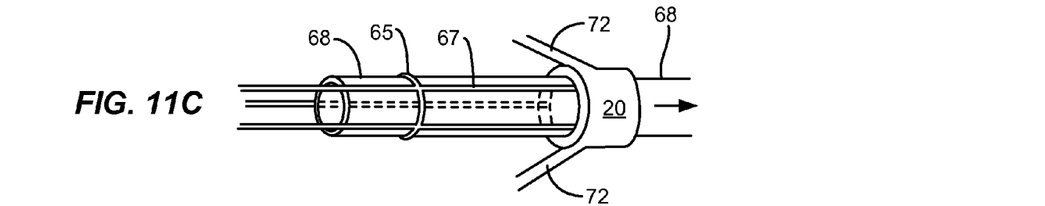
Figure 11D:
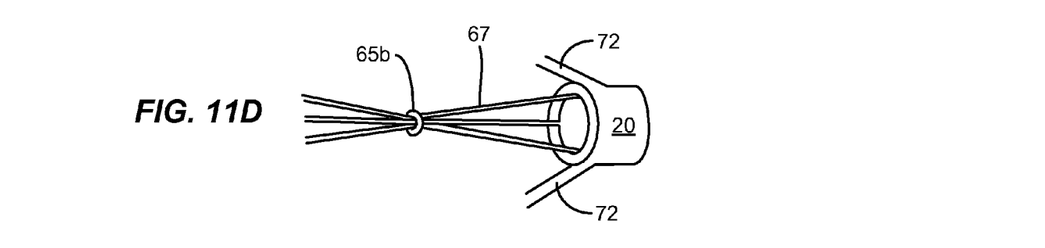

FIGS. 11A-11D illustrate use of the elastic binding ring (65) a method to secure the straps/tethers (67) to a focal point within a pyloric sphincter (74). The elastic binding ring (65) is pre-loaded over an inner tube (68) which holds the ring (65) open as shown in FIG. 11B. One elastic binding ring is illustrated put two or more rings could be used to create a bound linear segment (rather than a sole focal point). The purpose of the constraint is to reduce or eliminate stress on the pyloric sphincter (74) that may result from unbound tethers/straps that traverse the pyloric opening.

Figure 12A:
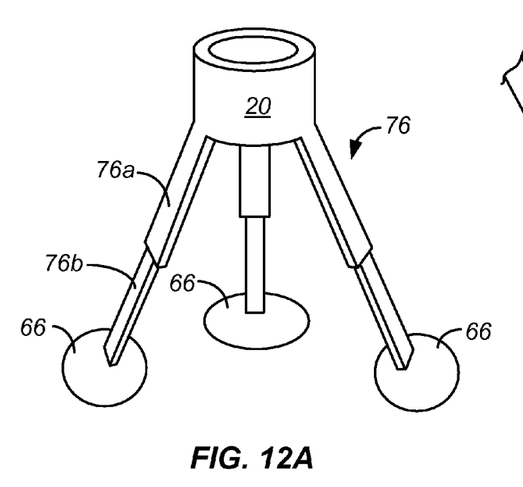
FIGS. 12A and 12B illustrate a further exemplary embodiment of a tripod base of a suprapyloric anchor assembly having self-adjusting struts constructed in accordance with the principles of the present invention.
Figure 12B:
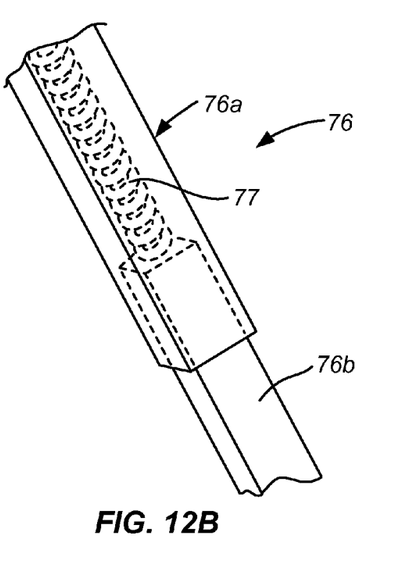

FIGS. 12A and 12B illustrate spring-loaded antral anchor legs (76) which absorb the impact of antral (lower stomach) contractions (also known as antral peristalsis or lower stomach contraction waves). The legs (76) comprise an upper portion (76a) and a lower portion (76b) coupled by spring (77), typically a coil spring, which can compress and extend as axial load varies. Alternatively, the antral anchor legs may have an "accordion-like" structure to absorb the impact of antral contraction waves.

Figure 13A:
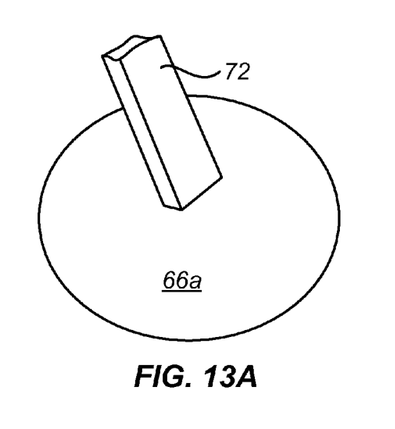
FIGS. 13A and 13B illustrate a further exemplary embodiment of a tripod base of a suprapyloric anchor assembly having gel-pad feet constructed in accordance with the principles of the present invention.
Figure 13B:
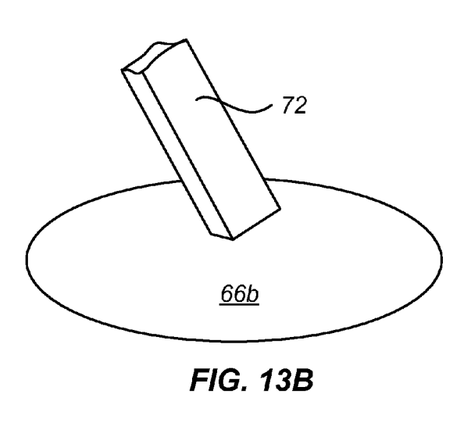

FIGS. 13A and 13B illustrate silicone gel footpads in the non-compressed state (66a) and compressed state (66b) which allows for distribution of force/pressure from the antral anchor legs on the antral (stomach) surface.

What is claimed is:

1. A suprapyloric anchor assembly comprising:
   an antral cap having at least three stabilizing members configured to reside in an antrum and engage tissue circumscribing a pyloric valve, wherein the stabilizing members comprise elongate legs joined to the collar at their proximal ends and having atraumatic distal ends to engage the tissue circumscribing the pyloric valve so that the legs form a tripod maintaining the antral cap above the pylorus and preventing passage of the antral cap into the pylorus;
   a duodenal member configured to reside at least partially in a duodenal bulb; and
   one or more tethers connecting the antral cap to the duodenal member, wherein said tether(s) is configured to allow passage of stomach contents through the pyloric valve.

2. The assembly of claim 1, wherein the antral cap comprises a collar with a central passage.

3. The assembly of claim 1, wherein the legs are self-opening so that the legs may be radially constrained to have a reduced collective diameter to facilitate introduction and may be released from constraint to diverge and form the tripod where the atraumatic distal ends are spaced-apart.

4. The assembly of claim 1, wherein the legs are spring-loaded to absorb antral contractions.

5. The assembly of claim 1, wherein the duodenal member comprises a funnel section configured to reside in the duodenal bulb and a cylindrical sleeve membrane configured to reside in the duodenum below the duodenal bulb.

6. The assembly of claim 1, further comprising at least one gastric balloon connectable to the antral cap.

7. The assembly of claim 1, further comprising at least one constraining band configured to circumscribe the tethers at a location within the pyloric sphincter.

8. A method for deploying a suprapyloric anchor, said method comprising:
   providing a suprapyloric anchor comprising an antral cap connected to a duodenal member by one or more tethers;
   endoscopically introducing the suprapyloric anchor with three constrained stabilizing members;
   positioning the duodenal member in a duodenal bulb with the tethers passing through a pyloric valve;
   releasing the duodenal member in a duodenal bulb with the tethers passing through a pyloric valve;

expanding the stabilizing members to form a tripod with atraumatic distal tips engaging tissue circumscribing the pyloric valve, wherein the stabilizing members hold the antral cap above the pylorus to allow passage of stomach contents through the pyloric valve;

wherein the duodenal member is tensioned to hold the stabilizing members against the circumscribing tissue.

9. A method as in claim 8, further comprising inflating at least one gastric balloon attached to the suprapyloric anchor.

10. A method as in claim 9, further comprising deploying a duodenal sleeve attached to the suprapyloric anchor.

11. A method as in claim 8, wherein endoscopically introducing comprises locating the suprapyloric anchor coaxially over an endoscope and passing the anchor and endoscope through an overtube which has been transesophageally introduced into the gastric cavity.

12. A method as in claim 8, further comprising radially constraining the tethers at the location where they pass through the pyloric valve.

13. A method as in claim 8, wherein the three constrained stabilizing members of the suprapyloric anchor are configured to absorb antral contractions.

\* \* \* \* \*